United States Patent [19]

Dolphin

[11] Patent Number: 4,677,206
[45] Date of Patent: Jun. 30, 1987

[54] 2-HYDROXY ETHYL BENZYL PYRIDINIUM COMPOUNDS

[75] Inventor: John M. Dolphin, East Boston, Mass.

[73] Assignee: Polaroid Corporation, Patent Dept., Cambridge, Mass.

[21] Appl. No.: 831,484

[22] Filed: Feb. 20, 1986

Related U.S. Application Data

[62] Division of Ser. No. 763,817, Aug. 8, 1985, Pat. No. 4,588,672.

[51] Int. Cl.$^4$ .................. C07D 211/70; C07D 211/82; C07D 213/24; C07D 213/53
[52] U.S. Cl. .................................... 546/344; 546/329; 546/334; 546/331; 546/338; 540/133; 549/394; 556/33
[58] Field of Search ................ 546/344, 329, 334, 331

[56] References Cited

U.S. PATENT DOCUMENTS

| | | |
|---|---|---|
| 3,173,786 | 3/1965 | Green et al. .......................... 546/344 |
| 3,649,265 | 3/1972 | Stewart ................................ 546/344 |
| 3,816,125 | 6/1974 | December et al. ................... 546/344 |
| 4,109,000 | 8/1978 | Tanabe et al. ....................... 546/344 |
| 4,543,317 | 9/1985 | Mehta et al. ........................ 546/344 |

OTHER PUBLICATIONS

Beyermann, et al., Rec. Trav. Chem. 75, 1956, pp. 63-74.
Weber, H., CA, 83:96964e.

Primary Examiner—Henry R. Jiles
Assistant Examiner—Robert C. Whittenbaugh
Attorney, Agent, or Firm—Gaetano D. Maccarone

[57] ABSTRACT

There is described a photographic system wherein development of an exposed photosensitive element with an aqueous alkaline photographic developing composition is effected in the presence of a compound which releases a quaternary in alkaline environment. Photographic products and processes utilizing such compounds are also disclosed.

3 Claims, 1 Drawing Figure

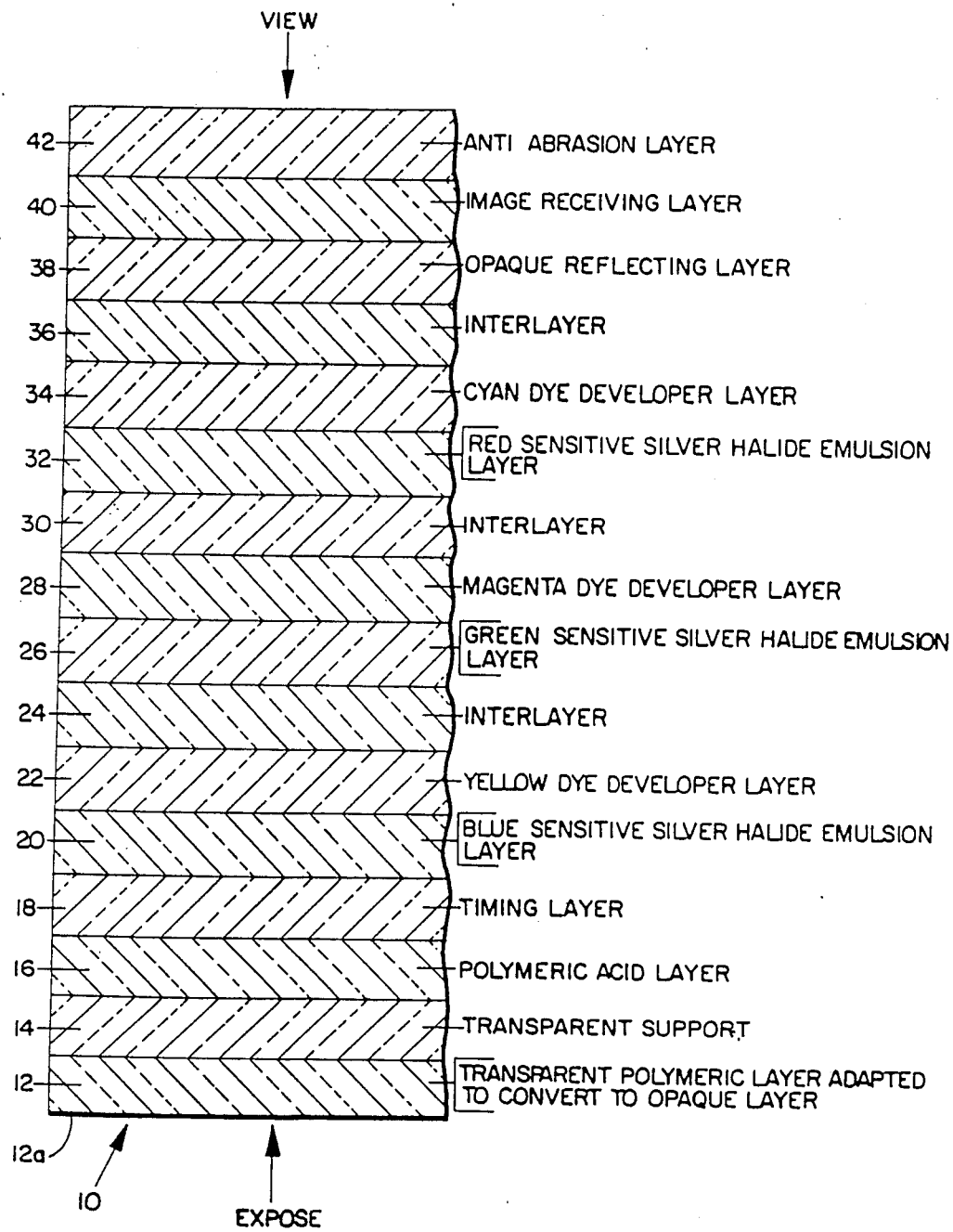

2-HYDROXY ETHYL BENZYL PYRIDINIUM COMPOUNDS

This is a division of application Ser. No. 763,817, filed Aug. 8, 1985 now U.S. Pat. No. 4,588,672.

BACKGROUND OF THE INVENTION

The application relates to a photographic system, including photographic products and processes, which utilize compounds capable of releasing a quaternary upon contact with an aqueous alkaline processing composition. The application also relates to novel compounds.

In various photographic systems for forming images, whether in black and white or in color, it is often desirable to include in the photographic film unit one or more of the various photographic reagents required for develoment and/or to enhance image quality. This practice extends to both conventional systems for forming negative images and also to various systems such as diffusion transfer wherein a positive image in silver or in color is obtained. In many instances the photographic reagent may be contained initially in either the processing composition applied for development and image formation or in the film unit itself. The latter embodiment is typically preferred so as to reduce the number of ingredients required in the processing composition. In other instances the particular photographic reagent desired is not sufficiently stable in alkali to provide the requisite shelf life for the processing composition or the reagent is not compatible and/or reacts with another reagent in the processing composition and therefore must be contained initially in the film unit. In still other instances the reagents must be provided at some particular time in the development process which requires that it be present in a specified layer or in specified proximity to another layer in the film unit.

In all the foregoing instances it is desirable that the reagent be contained in the desired layer or layers of the film unit in a form that is stable and non-migratory or non-diffusible and yet available when it is required at a particular time in the development process. To accomplish this result it is known in the art to attach to the particular photographic reagent a blocking moiety which prevents the reagent from reacting with other photographic materials present in the film unit or migrating or diffusing prior to the time when photographic development is effected but which will release the photographic reagent at the desired time such as by reaction with the aqueous alkaline processing composition.

The present application relates to a photographic system wherein development of an exposed photosensitive element is carried out in the presence of a compound which provides a controlled release of a quaternary during the development process and to novel compounds.

SUMMARY OF THE INVENTION

It is therefore an object of the invention to provide a novel photographic system.

It is another object of the invention to provide a system which utilizes a compound capable of releasing a quaternary during development of an exposed photosensitive element.

Still another object is to provide novel photographic products and processes.

Yet another object is to provide novel compounds.

BRIEF SUMMARY OF THE INVENTION

These and other objects and advantages are accomplished in accordance with the invention by providing a photographic system wherein development of an exposed photosensitive element with an aqueous alkaline processing composition is carried out in the presence of a compound represented by the formula

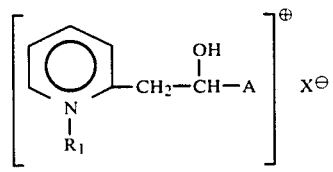

wherein $R_1$ is $-(CH_2)n-R_2$; $R_2$ can be hydrogen, alkyl, preferably having from 1 to 6 carbon atoms, or aryl such as phenyl or phenyl substituted with any photographically acceptable substituents such as electron withdrawing groups, e.g., trifluoromethyl, cyano, fluorine, bromine, chlorine or iodine, etc., or electron donating groups such as alkyl, alkoxy, e.g., methoxy and benzyloxy, amino, etc.; A is an aromatic group such as phenyl, naphthyl or phenyl or naphthyl substituted with any suitable electron withdrawing or electron donating groups such as those described above; X is a photographically acceptable anion such as radicals of bromine, N-toluene sulfonyl anthranilate, naphthalene sulfonate, lauryl sulfate, and n is an integer of from 1 to 6.

Where $R_2$ is aryl, it is possible to change the release rate of the material by appropriately substituting the $R_2$ group. An electron withdrawing substituent typically would increase the release rate whereas an electron donating substituent typically will decrease the release rate.

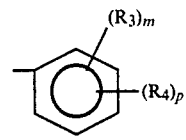

where $R_3$ and $R_4$ can each independently be hydrogen, an electron donating group such as nitro, amino, alkyl, preferably having from 1 to 6 carbon atoms, alkoxy, preferably having from 1 to 6 carbon atoms, e.g., methoxy and benzyloxy, etc.; an electron withdrawing group such as any described above; or $-NHSO_2R_5$ wherein $R_5$ can be alkyl, preferably having from 1 to 16 carbon atoms or aryl such as phenyl or substituted phenyl; and m and p are each independently 0 or 1.

The substituent(s) on the aromatic ring A also affect the release rate of the compound. Generally, the electron donating group will increase the release rate whereas the electron withdrawing groups decrease the rate. It is preferred to substitute the ring in the para position and it is particularly preferred to do so with an electron donating group since this embodiment provides the fastest release. It should be noted that typically the effect on the release rate of $R_3$ and $R_4$ is greater than that of substituents attached to $R_2$ when $R_2$ is aryl.

It is known in the art, as taught by U.S. Pat. No. 3,173,786 that quaternary groups can function as development accelerators in diffusion transfer photographic systems which utilize dye developers as the image dye-providing materials. It is also disclosed that, in such systems, quaternary groups which include a reactive methyl group, i.e., a methyl group which in alkali is capable of forming a methylene base, can also provide improved color separation, i.e., the transfer of the dye developers is more closely controlled by the silver halide emulsion with which each is associated. The compounds within Formula A cleave in alkaline compositions to provide a controlled release of such a methylene base.

The rate of release of the quaternary is dependent upon the hydroxyl ion concentration of the processing composition used to process the photographic elements and is also temperature dependent, that is, more is released as the temperature at which processing of the photographic element is effected rises.

BRIEF DESCRIPTION OF THE DRAWING

For a better understanding of the invention as well as other objects and further features thereof, reference is made to the followng detailed description of various preferred embodiments thereof taken in conjunction with the accompanying drawing wherein the figure is a partially schematic, cross-sectional view of one embodiment of a film unit according to the invention.

DESCRIPTION OF THE PREFERRED EMBODIMENTS

A class of preferred compounds for use according to the invention is represented by the formula

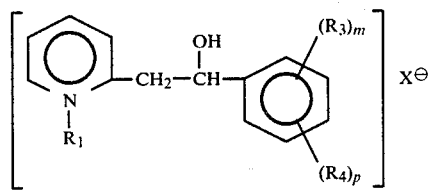

wherein $R_1$, $R_3$, $R_4$, X, m and p are as previously defined. Specific preferred compounds within this formula are:

| COMPOUND | $R_1$ | $R_3$ | $R_4$ | X |
|---|---|---|---|---|
| 1 | –(phenyl)–(CH$_2$)$_2$– | (m) –OCH$_2$–(phenyl) | | CF$_3$SO$_3^\ominus$ |
| 2 | –(phenyl)–(CH$_2$)$_2$– | | (p) –OCH$_3$ | CF$_3$SO$_3^\ominus$ |
| 3 | –(phenyl)–(CH$_2$)$_2$– | | (p) –NO$_2$ | CF$_3$SO$_3^\ominus$ |
| 4 | –(phenyl)–(CH$_2$)$_2$– | | (p) –NHSO$_2$(CH$_2$)$_2$CH$_3$ | CF$_3$SO$_3^\ominus$ |
| 5 | –(phenyl)–(CH$_2$)$_2$– | (O) –OCH$_3$ | | CF$_3$SO$_3^\ominus$ |
| 6 | –(phenyl)–CH$_2$– | (O) –OCH$_3$ | | Br$^\ominus$ |

-continued

| COMPOUND | $R_1$ | $R_3$ | $R_4$ | X |
|---|---|---|---|---|
| 7 | 2-methylbenzyl (o-CH₃-C₆H₄-CH₂-) | | (p) —NO₂ | $Br^\ominus$ |
| 8 | C₆H₅-(CH₂)₂- | (O) —OCH₃ | (p) Br | $CF_3SO_3^\ominus$ |
| 9 | C₆H₅-CH₂- | | (p) —NSO₂(C₆H₄-CH₃)(CH₂C₆H₅) | $Br^\ominus$ |
| 10 | 2-methylbenzyl | | (p) —NHSO₂-C₆H₄-CH₃ | $Br^\ominus$ |
| 11 | 2-methylbenzyl | | (p) —NO₂ | 2-naphthalenesulfonate ($SO_3^\ominus$) |
| 12 | C₆H₅-CH₂- | | (p) —NHSO₂-C₆H₄-CH₃ | $Br^\ominus$ |
| 13 | 2-methylbenzyl | | (p) —NHSO₂(CH₂)₁₅CH₃ | $Br^\ominus$ |
| 14 | 2-methylbenzyl | | (p) —NHSO₂-C₆H₄-(CH₂)₁₁CH₃ | $Br^\ominus$ |
| 15 | C₆H₅-CH₂- | | (p) —NHSO₂(CH₂)₁₅CH₃ | $Br^\ominus$ |
| 16 | 2-methylbenzyl | | (p) —OCH₃ | $Br^\ominus$ |

-continued

| COMPOUND | R₁ | R₃ | R₄ | X |
|---|---|---|---|---|
| 17 | ⌬—(CH₂)₂— | (O) | —OCH₃ | CF₃SO₃⁻ |
| 18 | ⌬—(CH₂)₂— | | | CF₃SO₃⁻ |

Another class of preferred compounds for use according to the invention is represented by the formula

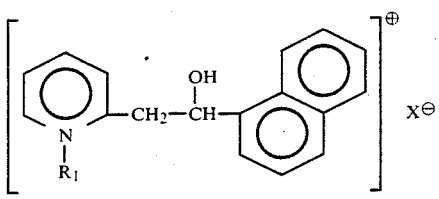

wherein R₁ and X are as previously defined.

The compounds may be prepared according to reactions which are known to those skilled in the art. Generally, the compounds can be made by the condensation of picoline with an aldehyde in the presence of a base where required. Typically the picoline is initially reacted with butyl lithium to give 2-picolyl lithium and the latter is reacted with the appropriate aldehyde followed by alkylation.

These compounds may be present in photographic elements in any appropriate location and in any amount which is required to accomplish their intended purpose. The amount necessary in any particular instance is dependent upon a number of factors such as, for example, the compound utilized, the type of photographic element, the location of the compound in the photographic element and the result desired. Routine scoping tests may be used to ascertain the concentration which is appropriate for any given photographic element. According to a preferred embodiment of the invention there are provided diffusion transfer photographic film units as will be discussed more in detail below herein. In such photographic film units the compounds may be incorporated in the photosensitive element and/or the image receiving element. The compounds may be used in any photographic system wherein the release of a quaternary during development of an exposed photosensitive element is desired, including photographic systems for forming images in black and white or in color and those wherein the final image is a silver image or one formed by other image-forming materials. Further, where appropriate, the compounds may be utilized in various layers of a multilayer photographic system in varying concentrations to ensure the desired distribution of the quaternary during processing.

The compounds utilized according to the invention may be used in conjunction with any photographic emulsion. In a preferred embodiment the compounds are utilized in diffusion transfer photographic systems, particularly those which include a negative working silver halide emulsion, i.e., one which develops in the areas of exposure. Further, these compounds may be used in association with any image dye-providing materials. In a particularly preferred embodiment the diffusion transfer photographic film elements of the invention include one or more image dye-providing materials which may be initially diffusible or nondiffusible. In diffusion transfer photographic systems the image dye-providing materials which can be utilized generally may be characterized as either (1) initially soluble or diffusible in the processing composition but which are selectively rendered nondiffusible imagewise as a function of development; or (2) initially insoluble or nondiffusible in the processing composition but which selectively provide a diffusible product imagewise as a function of development. The image dye-providing materials may be complete dyes or dye intermediates, e.g., color couplers. The requisite differential in mobility or solubility may be obtained, for example, by a chemical reaction such as a redox reaction, a coupling reaction or a cleavage reaction. In a particularly preferred embodiment of the invention the image dye-providing materials are dye developers which are initially diffusible materials. The dye developers contain, in the same molecule, both the chromophoric system of a dye and a silver halide developing function as is described in U.S. Pat. No. 2,983,606.

Other image dye-providing materials which may be used include, for example, initially diffusible coupling dyes such as are useful in the diffusion transfer process described in U.S. Pat. No. 3,087,817 which are rendered nondiffusible by coupling with the oxidation product of a color developer; initially nondiffusible dyes which release a diffusible dye following oxidation, sometimes referred to as "redox dye releaser" dyes, described in U.S. Pat. Nos. 3,725,062 and 4,076,529; initially nondiffusible image dye-providing materials which release a diffusible dye following oxidation and intramolecular ring closure as are described in U.S. Pat. No. 3,433,939 or those which undergo silver assisted cleavage to release a diffusible dye in accordance with the disclosure of U.S. Pat. No. 3,719,489; and intially nondiffusible image dye-providing materials which release a diffusible dye following coupling with an oxidized color developer as described in U.S. Pat. No. 3,227,550.

In the diffusion transfer photographic film units of the invention a quaternary may be included in the processing composition and a quaternary-releasing compound within Formula A incorporated in the photosensitive element. The quaternary which is released may be the same as or different than the quaternary in the processing composition.

The compounds may be incorporated into the photographic elements by any suitable technique. The compounds can be incorporated in the photographic element typically by being coated from a water or oil dispersion and the layer(s) in which they reside typically include a binder material such as gelatin or the like.

In a preferred embodiment of the invention, the compounds are utilized in diffusion transfer photographic film units in conjunction with initially diffusible dye developers as the image dye-providing materials. As described in U.S. Pat. No. 2,983,606 a photosensitive element containing a dye developer and a silver halide emulsion is photoexposed and a processing composition applied thereof, for example, by immersion, coating, spraying, flowing, etc., in the dark. The exposed photosensitive element is superposed prior to, during, or after the processing composition is applied, on a sheet-like support element which may be utilized as an image-receiving element. In a preferred embodiment, the processing composition is applied to the exposed photosensitive element in a substantially uniform layer as the photosensitive element is brought into superposed relationship with the image-receiving layer. The processing composition, positioned intermediate the photosensitive element and the image-receiving layer, permeates the emulsion to initiate development. The dye developer is immobilized or precipitated in exposed areas as a consequence of the development. In unexposed and partially exposed areas of the emulsion, the dye developer is unreacted and diffusible and thus provides an imagewise distribution of unoxidized dye developer, diffusible in the processing composition, as a function of the point-to-point degree of exposure of the silver halide emulsion. At least part of this imagewise distribution of unoxidized dye developer is transferred, by imbibition, to a superposed image-receiving layer or element, said transfer substantially excluding oxidized dye developer. The image-receiving layer receives a depthwise diffusion, from the developed emulsion, of unoxidized dye developer without appreciably disturbing the imagewise distribution thereof to provide a reversed or positive color image of the developed image. The image-receiving element may contain agent adapted to mordant or otherwise fix the diffused, unoxidized dye developer. In a preferred embodiment of said U.S. Pat. No. 2,983,606 and in certain commercial applications thereof, the desired positive image is revealed by separating the image-receiving layer from the photosensitive element at the end of a suitable imbibition period. Alternatively, as also disclosed in said U.S. Pat. No. 2,983,606, the image-receiving layer need not be separated from its superposed contact with the photosensitive element, subsequent to transfer image formation, if the support for the image-receiving layer, as well as any other layers intermediate said support and image-receiving layer, is transparent and a processing composition containing a substance, e.g., a white pigment, effective to mask the developed silver halide emulsion or emulsions is applied between the image-receiving layer and said halide emulsion or emulsions.

Dye developers, as noted in said U.S. Pat. No. 2,983,606, are compounds which contain, in the same molecule, both the chromophoric system of a dye and also a silver halide developing function. By "a silver halide developing function" is meant a grouping adapted to develop exposed silver halide. A preferred silver halide development function is a hydroquinonyl group. In general, the development function includes a benzenoid developing function, that is, an aromatic developing group which forms quinonoid or quinone substances when oxidized.

Multicolor images may be obtained using dye developers in diffusion transfer processes by several techniques. One such technique contemplates obtaining multicolor transfer images utilizing dye developers by employment of an integral multilayer photosensitive element, such as is disclosed in the aforementioned U.S. Pat. No. 2,983,606 and in U.S. Pat. No. 3,345,163, wherein at least two selectively sensitized photosensitive strata, superposed on a single support, are processed, simultaneously and without separation, with a single common image-receiving layer. A suitable arrangement of this type comprises a support carrying a red-sensitive silver halide emulsion stratum, a green-sensitive silver halide emulsion stratum and a blue-sensitive silver halide emulsion stratum, said emulsions having associated therewith respectively, for example, a cyan dye developer, a magenta dye developer and a yellow dye developer. The dye developer may be utilized in the silver halide emulsion stratum, for example, in the form of particles, or it may be disposed in a stratum behind the appropriate silver halide emulsion strata. Each set of silver halide emulsion and associated dye developer strata may be separated from other sets by suitable interlayers, for example, by a layer or stratum of gelatin or polyvinyl alcohol. In certain instances, it may be desirable to incorporate a yellow filter in front of the green-sensitive emulsion and such yellow filter may be incorporated in an interlayer. However, where desirable, a yellow dye developer of the appropriate spectral characteristics and present in a state capable of functioning as a yellow filter may be so employed and a separate yellow filter omitted.

Particularly useful products for obtaining multicolor dye developer images are disclosed in U.S. Pat. No. 3,415,644. This patent discloses photographic products wherein a photosensitive element and an image-receiving are maintained in fixed relationship prior to exposure, and this relationship is maintained as a laminate after processing and image formation. In these products, the final image is viewed through a transparent (support) element against a light-reflecting, i.e., white background. Photoexposure is made through said transparent element and application of the processing composition provides a layer of light-reflecting material to provide a white background. The light-reflecting material (referred to in said patent as an "opacifying agent")

is preferably titanium dioxide, and it also performs an opacifying function, i.e., it is effective to mask the developed silver halide emulsions so that the transfer image may be viewed without interference therefrom, and it also acts to protect the photoexposed silver halide emulsions from post-exposure fogging by light passing through said transparent layer if the photoexposed film unit is removed from the camera before image formation is completed.

U.S. Pat. No. 3,647,437 is concerned with improvements in products and processes disclosed in said U.S. Pat. No. 3,415,644, and discloses the provision of light-absorbing materials to permit such processes to be performed, outside of the camera in which photoexposure is effected, under much more intense ambient light conditions. A light-absorbing material or reagent, preferably a pH-sensitive phthalein dye, is provided so positioned and/or constituted as not to interfere with photoexposure but so positioned between the photoexposed silver halide emulsions and the transparent support during processing after photoexposure as to absorb light which otherwise might fog the photoexposed emulsions. Furthermore, the light-absorbing material is so positioned and/or constituted after processing as not to interfere with viewing the desired image shortly after said image has been formed. In the preferred embodiments, the light-absorbing material, also sometimes referred to as an optical filter agent, is initially contained in the processing composition together with a light-reflecting material, e.g., titanium dioxide. The concentraion of the light-absorbing dye is selected to provide the light transmission opacity required to perform the particular process under the selected light conditions.

In a particularly useful embodiment, the light-absorbing dye is highly colored at the pH of the processing composition, e.g., 13-14, but is substantially non-absorbing of visible light at a lower pH, e.g., less than 10-12. This pH reductionmay be effected by an acid-reacting reagent appropriately positioned in the film unit, e.g., in a layer between the transparent support and the image-receiving layer.

The dye developers are preferably selected for their ability to provide colors that are useful in carrying out subtractive color photography, that is, the previously mentioned cyan, magenta and yellow. The dye developers employed may be incorporated in the respective silver halide emulsion or, in the preferred embodiment, in a separate layer behind the respective silver halide emulsion, and such a layer of dye developer may be applied by use of a coating solution containing the respective dye developer distributed, in a concentration calculated to give the desired coverage of dye developer per unit area, in a film-forming natural, or synthetic, polymer, for example, gelatin, polyvinyl alcohol, and the like, adapted to be permeated by the processing composition.

Other diffusion transfer products and processes in which the dye developers of the present invention may be utilized are described in U.S. Pat. Nos. 3,573,043 and 3,594,165. For convenience, the entire disclosure of each of the six patents referred to immediately above is hereby incorporated by reference herein.

A particularly useful film unit according to the invention is one wherein the photosensitive element includes a light-reflecting layer between the silver halide layer and the image dye-providing material layer (as described in Canadian Patent 668,592), the substrate of the photosensitive element carries the polymeric acid neutralizing layer which in turn carries the timing layer (as described in U.S. Pat. No. 3,573,043) and the processing composition includes an oximated polydiacetone acrylamide thickening agent (as described in U.S. Pat. No. 4,202,694).

In the FIGURE there is shown another preferred diffusion transfer film unit of the invention wherein the film unit 10 comprises a transparent support 14 carrying on a first side thereof a layer 12 of a transparent polymeric material adapted to convert to an opaque condition when contacted by an aqueous alkaline processing composition. On the opposed side of support layer 14 is shown a polymeric acid-reacting layer 16, timing layer 18, a blue sensitive silver halide emulsion layer 20, a yellow dye developer layer 22, an interlayer 24, a green sensitive silver halide emulsion layer 26, a magenta dye developer layer 28, an interlayer 30, a red sensitive silver halide emulsion layer 32, a cyan dye developer layer 34, an interlayer 36, an opaque/reflective layer 38 (which preferably contains a white pigment such as titanium dioxide to provide a white background against which the image is viewed and an opacification agent such as carbon black), an image receiving layer 40 and an anti-abrasion layer 42.

Photoexposure of the silver halide emulsion layers is effected through the transparent polymeric layer 12 and through transparent support 14 and the layer carried thereon, i.e., the polymeric acid layer 16 and the spacer or timing layer 18, which layers are also transparent, the film unit being so positioned within the camera that light admitted through the camera exposure or lens system is incident upon the outer or exposure surface 12a of the polymeric layer 12.

After photoexposure, the film unit is developed such as by immersing it in an aqueous alkaline processing composition. After a suitable imbibition period, e.g., in the range of about 40 to 120 seconds, the transparent polymeric layer 12 is converted by the alkaline processing composition to a highly colored, or opaque, layer. In addition, development of emulsion layers 20, 26 and 32 is initiated by contact with the processing composition. If the film unit is removed from the processing composition to conditions of ambient light, the still photosensitive and developing emulsion layers thereof are protected against additional photoexposure by ambient and environmental light through transparent support 14 by the now opaque layer 12. The emulsion layers are protected against additional photoexposure from the opposed, or image-viewing, side of the film unit by opaque reflective layer 38.

In exposed and developed areas, the dye developers are oxidized as a function of the silver halide development and are immobilized. Unoxidized dye developer associated with undeveloped and partially developed areas remains mobile and is transferred to the image-receiving layer 40 to provide the desired positive image therein.

Permeation of the alkaline processing composition through the several layers of the film unit is controlled so that the process pH is maintained at a high enough level to effect the requisite development and image transfer and to convert polymeric layer 12 to a highly colored form after which pH reduction is effected as a result of alkali permeation into the polymeric acid layer 16 such that the pH is reduced to a level which stops further dye transfer. Layer 12, after having been rendered opaque by the action of alkali, remains opaque notwithstanding this pH reduction. The image present in image-receiving layer 40 is viewed though the anitabrasion layer 42 against the reflecting layer 38 which provides an essential white background for the dye image and also effectively masks from view the developed silver halide emulsion layers of dye develoer immobilized therein or remaining in the dye developer layers.

In the embodiment illustrated in the FIGURE image receiving layer 40 and reflecting layer 38 against which the image is viewed are shown as layers of the film unit 10. While this is a particularly useful and preferred embodiment, image formation can be accomplished in a separate image receiving element comprising a transparent or opaque (e.g., baryta) support and an image receiving layer. The image receiving element may be brought into superposed relation with a photosensitive element comprising layers 12 through 38, either before or after photoexposure thereof. Polymeric layer 12 can be rendered opaque and development can be initiated by contact with an aqueous alkaline processing composition. The image-receiving element can be left intact for viewing through the transparent support thereof, a reflection print against reflective layer 38. Alternatively, the image-receiving element can be separated for a viewing of a transparency or reflection print, respectively in the case of a transparent or opaque image-receiving element support.

According to another embodiment, transparent polymeric layer 12 can, if desired, be positioned between transparent support 14 and polymeric acid layer 16. It will be appreciated, however, that owing to the amount of time required for alkali to permeate the several layers of the film unit so as to permit conversion of the transparent layer 12 to an opaque layer, the positioning shown in the FIGURE is preferred. A quaternary nitrogen-containing polymer suitable for use in layer 12 is disclosed in U.S. Pat. No. 4,452,878.

It should be noted here that other opacification systems may be used in layer 12. Further, it should also be recognized that photoexposure and processing of the film unit can be carried out in the dark in which case layer 12 is not required.

The invention will now be desired further in detail with respect to specific preferred embodiments by way of examples, it being understood that these are illustrative only and the invention is not intended to be limited to the materials, conditions, process parameters, etc., which are recited therein.

EXAMPLE I

A stainless steel bomb containing p-nitrobenzaldehyde (300g, 1.99 moles), α-picoline (650 ml, 6.59 moles) and distilled water (100 ml, 5.56 moles) was sealed and held in an oil bath at 140°–160° C. for 19 hours. It was cooled to room temperature and opened to the atmosphere. The contents of the reactor, a mass of crystals and some dark liquid, were added to one liter of a 60:40 methanol-water mixture and the resulting mixture stirred for two hours. The solid was recovered by filtration, washed with one liter of the same solvent mixture and dried under vacuum at 50° C. to give 383–396g (79%–82% yield) of

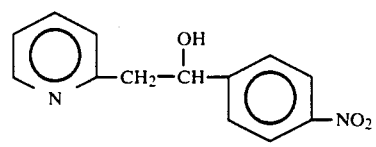

4-nitrophenyl-(α-picolyl)-carbinol.

The carbinol (210g, 0.86 mole) was suspended in one liter of $CF_3CH_2OH$ along with 5g of 10% Pd-C and the mixture agitated with a mechanical rocker under 6 atmospheres of hydrogen for 30 hours. The mixture was then filtered through diatomaceous earth and the filtrate evaporated under vacuum. The crude solid product was recrystallized from hot ethyl acetate to give 143g (77% yield)

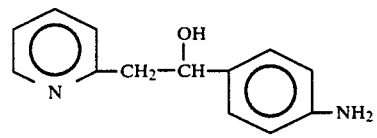

as off-white prisms.

The amine (188g, 0.88 mole) was stirred in 750 ml of pyridine at 0° C. under a calcium sulfate drying tube. Tosyl chloride (170g, 0.885 mole) was added to the solution in solid portions over 1¼hours. When addition was complete the reaction mixture was stirred at room temperature for one hour and then slowly poured into 8 liters of distilled water with vigorous stirring. The product was collected by suction filtration, washed with approximately 2 liters of water and then with 95% ethanol and pressed to remove solvent. The solid was then recrystallized twice from hot 95% ethanol to give 284g (88% yield) of 4-p-toluene sulfonamidophenyl(α-picolyl)-carbinol

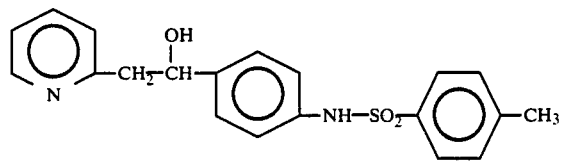

as white plates.

The 4-p-toluene sulfonamidophenyl(α-picolyl)-carbinol (123g, 0.338 mole) was suspended in 400 ml of sulfolane and stirred as o-methylbenzylbromide (64g, 46.3 ml, 0.345 mole) was added in a single portion. The resulting suspension was heated to 80° C. with stirring under nitrogen for 2½ hours during which time the solid dissolved and then reprecipitated turning yellow in color. The suspension was cooled somewhat and ethyl acetate (1.25 liters) was added with stirring. The solid was isolated by suction filtration and pressed to remove solvent. The solid was resuspended with stirring in 750 ml of acetonitrile and filtered again. The solid was washed with 50% acetonitrile-methanol, then with acetonitrile and finally with diethyl ether and vacuum dried at room temperature to give 135g (72% yield) of

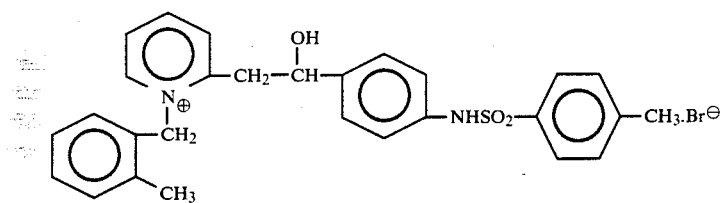

a pale yellow powder.

The structure of the product was confirmed by a $^{13}$C NMR spectrum. NMR [CDCL$_3$, (CD$_3$)$_2$S =O]δ2.19 (3H, S), 2.22 (3H, S), 3.25 (2H, n), 4.9 (1H, br t), 5.95 (2H, s), 6.4 (1.H, d, J =8Hz), 6.7–8.2 (13H, n), 8.34 (1H, t, J =7Hz), 8.8 (1H, d, J =7Hz), 9.9 (1H, s). The mass spectrum showed a cation with m/e=473.

EXAMPLE II

As a control a film unit was prepared by coating on a transparent subcoated polyethylene terephthalate film base the following layers:

1. an antistatic layer made up of about 500 mg/m$^2$ of sodium cellulose sulfate and about 150 mg/m$^2$ of potassium chloride;

2. a polymeric acid layer of approximately 9 parts by weight of a ½ butyl ester of polyethylene/maleic anhydride copolymer and 1 part of polyvinyl butyral coated at a coverage of about 16000 mg/m$^2$;

3. a timing layer coated at a coverage of about 2500 mg/m$^2$ of a 34-30-15-14-4-3 hexapolymer of diacetone acrylamide (DAA), butyl acrylate (BA), carbomethoxymethyl acrylate (CMA), ethyl acrylate (EA), acrylic acid (AA) and methyl methacrylate (MMA);

4. a blue sensitive silver iodobromide emulsion layer comprising about 598 mg/m$^2$ of silver (0.2 micron), about 299 mg/m$^2$ of silver (0.5 micron), about 598 mg/m$^2$ of silver (1.3 microns) and about 746 mg/m$^2$ of gelatin;

5. a yellow dye developer layer comprising about 1000 mg/m$^2$ of a yellow dye developer represented by the formula

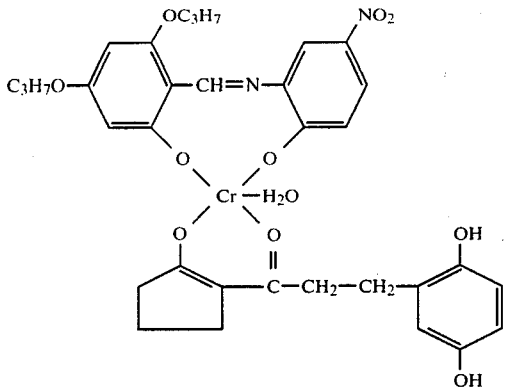

about 489 mg/m$^2$ of gelatin; about 100 mg/m$^2$ of 4'-methylphenylhydroquinone; and about 30 mg/m$^2$ of the methyl ethyl sulfone adduct of phenylmercaptotetrazole;

6. an interlayer made up of a 35-29-15-14-4-3 hexapolymer of DAA/BA/CMA/EA/AA/MMA coated at a coverage of about 1500 mgs/m$^2$, about 17 mgs/m$^2$ of succindialdehyde and about 23 mgs/m$^2$ of polyvinyl pyrollidone;

7. a green sensitive silver iodobromide emulsion layer comprising about 358 mgs/m$^2$ of silver (0.2 micron), about 179 mgs/m$^2$ of silver (0.5 micron), about 358 mgs/m$^2$ of silver (1.3 microns) and about 448 mgs/m$^2$ of gelatin;

8. a magenta dye developer layer comprising about 450 mgs/m$^2$ of a magenta dye developer represented by the formula

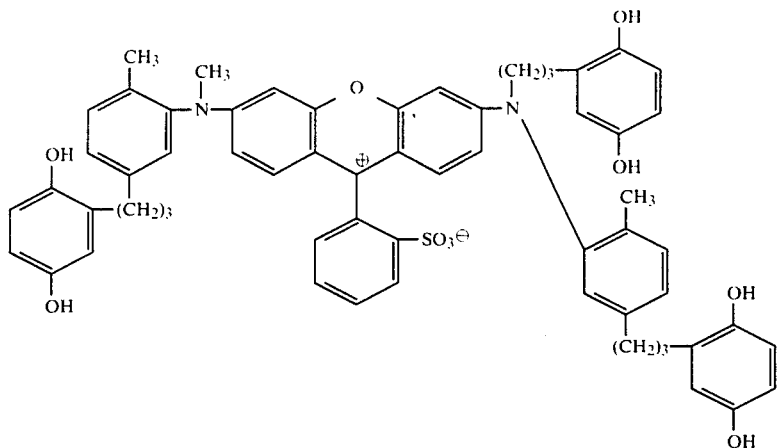

about 286 mgs/m² of gelatin, about 69 mgs/m² of 4'-methyl phenylhydroquinone and about 30 mgs/m² of the methyl ethyl sulfone adduct of phenylmercaptotetrazole;

9. an interlayer comprising about 2000 mgs/m² of the hexapolymer of layer 6, about 21 mgs/m² of succindialdehyde and about 60 mgs/m² of polyvinyl pyrrolidone;

10. a red sensitive silver iodobromide emulsion layer comprising about 289 mgs/m² of silver (0.2 micron), about 289 mgs/m² of silver (0.5 micron) about 289 mgs/m² of silver (1.3 microns) and about 433 mgs/m² of gelatin;

11. a cyan dye developer layer comprising about 425 mgs/m² of a cyan dye developer represented by the formula 12. an interlayer made up of a 37-30-14-11-5-3 hexapolymer of DAA/BA/EA/CMA/AA/MMA coated at a coverage of about 11 mgs/m² of succidialdehyde and about 30 mgs/m² of polyethyleneoxide;

13. an opacification layer comprising about 1000 mgs/m² of carbon black and about 275 mgs/m² of gelatin;

14. a reflection layer comprising about 11000 mgs/m² of titanium dioxide, about 1433 mgs/m² of polyethylene oxide, about 403 mgs/m² of gelatin, about 2200 mgs./m² of a 60-30-4-6 tetrapolymer of butyl acrylate, diacetone acylamide, styrene and methacrylic acid and about 1433 mgs/m² of Teflon 30 ®, a water based dispersion of hexafluoropropylene/tetrafluoropropylene copolymer particles;

15. an image receiving layer coated at a coverage of

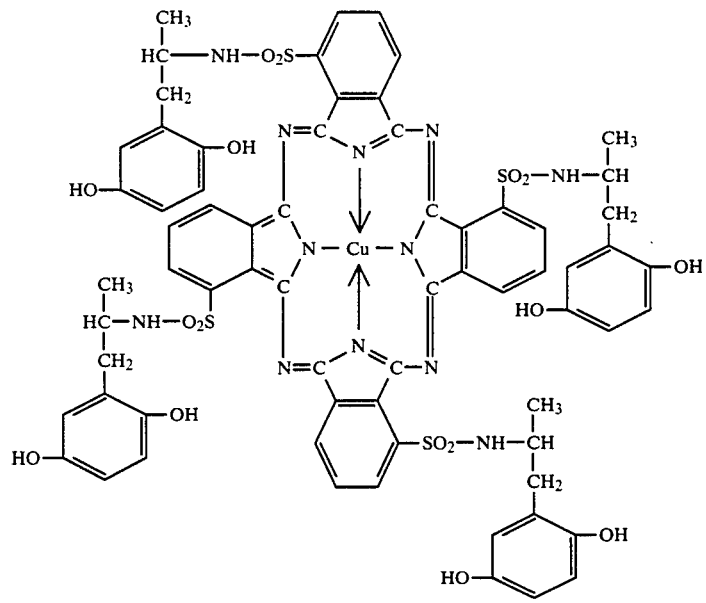

about 320 mgs/m² of gelatin, about 121 mgs/m² of 4'-methylphenylhydroquinone, about 41 mgs/m² of the methyl ethyl sulfone adduct of phenylmercaptotetrazole and about 25 mgs/m² of the cyclohexanoneoxime adduct of phenylmercaptotetrazole;

about 2000 mgs/m² of a graft copolymer comprising 4-vinylpyridine (4VP) and vinyl benzyl trimethylammonium chloride (TMQ) grafted onto hydroxyethylcellulose (HEC) at a ratio HEC/4VP/TMQ of 2.2/2.2/1, about 370 mgs/m² of gelatin and about 667 mgs/m² of a dihexyl ester of sodium sulfosuccinic acid; and 16. a topcoat layer of about 500 mg/m² of gelatin.

The film unit was exposed (12 mcs) in the dark to a test exposure target through the support and then laminated together with a processing element made up of a 4 mil thick corona treated polystyrene support having coated thereon 1. a layer made up of about 1500 mgs/m² of a copolymer of 3 parts 4-vinyl pyridine and 1 part vinyl benzyl trimethylammonium chloride and about 27 mgs/m² of 1,4-butanediol diglycidyl ether; and 2. a layer made up of about 3500 mgs/m² of kappa carrageenan, about 1512 mgs/m² of sodium hydroxide, about 1414 mgs/m² of potassium hydroxide and about 63,608 mgs/m² of water.

The laminate was allowed to remain in the dark for about five minutes and the red, green and blue $D_{max}$ and $D_{min}$ values for the neutral density columns were read on a densitometer.

A second control film unit was prepared and processed in the same manner with the only exception being that layer 2 of the processing element was made up of about 3500 mgs/m² of kappa carrageenan, about 1890 mgs/m² of sodium hydroxide, about 883 mgs/m² of potassium hydroxide, about 850 mgs/m² of phenethyl alpha-picolinium bromide and about 62,900 mgs/m² of water.

Film Units A and B according to the invention were prepared. These were identical to Control I except that the topcoat layer (16) of the photosensitive element included 1200 mgs/m² and 1400 mgs/m², respectively, of compound 10. The film units were processed as described above with a processing element such as that used to process Control I.

| FILM UNIT | | R | G | B |
|---|---|---|---|---|
| CONTROL I | $D_{max}$ | 2.13 | 2.53 | 2.63 |
| | $D_{min}$ | 0.23 | 0.23 | 0.47 |
| CONTROL II | $D_{max}$ | 1.99 | 2.35 | 1.91 |
| | $D_{min}$ | 0.19 | 0.21 | 0.28 |
| A | $D_{max}$ | 1.99 | 2.45 | 2.26 |
| | $D_{min}$ | 0.21 | 0.21 | 0.25 |
| B | $D_{max}$ | 2.00 | 2.56 | 2.28 |
| | $D_{min}$ | 0.20 | 0.21 | 0.26 |

The background areas of the Control I film unit had a yellowish color thereby indicating that the yellow dye developer was not completely controlled by the associated silver halide emulsion in the absence of a quaternary. The background areas of the Control II film unit were free of any yellow color showing that the quaternary in the processing composition had dramatically assisted in control of the yellow dye developer. The red, green and blue $D_{max}$ values for Control II were all significantly less than the corresponding values for Control I and the $D_{min}$ values were smaller, the blue being significantly smaller, showing that the quaternary assisted in the control of all three dye developers.

The background areas of film units A and B were virtually the same in appearance as those of Control II which indicates that the releasable quaternary compound of the invention was able to dramatically assist in the control of the yellow dye developer. Further, it can be seen that the green and blue $D_{max}$ values of both film units A and B were higher than the corresponding values for Control II with approximately the same $D_{min}$ values.

Although the invention has been described in detail with respect to various preferred embodiments thereof, these are intended to be illustrative only and the invention is not limited thereto but rather those skilled in the art will recognize that modifications may be made therein which are within the spirit of the invention and the scope of the appended claims.

What is claimed is:

1. A compound as represented by the formula

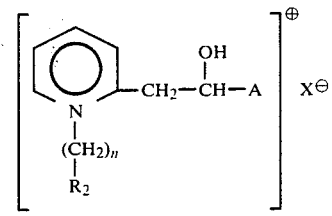

wherein $R_2$ is phenyl; A is phenyl or naphthyl; X is an anion; and n is an integer of from 1 to 6.

2. A compound represented by the formula

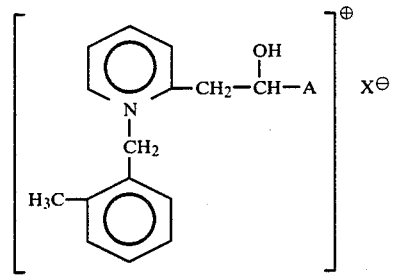

wherein A is phenyl or naphyl and X is anion.

3. A compound represented by the formula

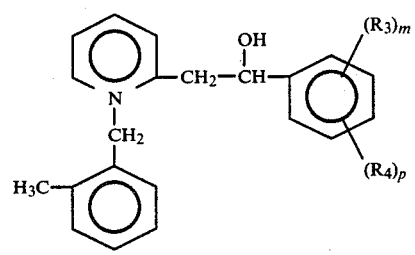

wherein Rhd 3 and $R_4$ each independently is hydrogen, nitro, amino, alkyl, alkoxy or $-NHSO_2R_5$; $R_5$ is alkyl or phenyl; and m and p each independently is 0 or 1.

* * * * *